United States Patent [19]
Webster et al.

[11] Patent Number: 6,020,360
[45] Date of Patent: Feb. 1, 2000

[54] ANTICANCER PROPERTY OF DITHIOLOPYRROLONES

[76] Inventors: John M. Webster, 5551 Molina Road, North Vancouver, Canada, V7R 4P3; Jianxiong Li, 117 Buckingham Dr., Port Moody, Canada, V3H 2T4; Genhui Chen, 725 Louis Riel, Simon Fraser University, Burnaby, Canada, V5A 1S6

[21] Appl. No.: 08/716,593

[22] Filed: Sep. 18, 1996

Related U.S. Application Data

[63] Continuation of application No. 08/716,593, Sep. 18, 1996.

[51] Int. Cl.$^7$ .................................................. A61K 31/40
[52] U.S. Cl. .......................................................... 514/421
[58] Field of Search .............................................. 514/421

[56] References Cited

PUBLICATIONS

Arnold, J. T. et al., 1995. *Cancer Research* 55:537–543.
Celmer, W. D. and I. A. Solomons 1955. *J. Amer. Chem. Soc.* 77:2861–2865.
Eisenman, W. et al., 1953. *Antibiotics and Chemotherapy* 3: 385–392.
Forst, S. and K. Nealson, 1996. *Microbiol. Rev.* 60:21–43.
Hagio, K. and Yoneda, N. 1974. *Bull. Chem. Soc. Japan.* 47:1484–1489.
Jimenez, A. et al., 1973, *Antimicrob. Ag. Chemother.* 729–738.
Li, J. et al., 1995. *J. Nat. Prod.* 58:1081–1085.
McInerney, B. V. et al., 1991. *J. Nat. Prod.* 54:774–784.
Menta R. G. and R. C. Moon, 1991. *Anticancer Research* 11:593–596.
Ninomiya, Y. T. et al., 1980. *Chem. Pharm. Bull.* 28:3157–3162.
Sharma, S. et al., 1994. *Cancer Research* 54:5848–5855.
Skehan, P. et al., 1990. *J. Natl. Cancer Inst* 82:1107–1118.
Stachel, H.D. et al. 1992. *Liebigs Ann. Chem.* 473–480. (Abstract only).
Tipper D.J. 1973, *J. Bacteriol.* 116:245–256.
Umezawa, H. et al. 1948. *Jap. Med. J.* 1:512–517.
von Daehne, W. et al., 1969. *J. Antibiotics* 22:233–235.
Mehta et al., Anticancer Res (1991) 11(2), 593–6 The Original Article to Follow in Due Course.

*Primary Examiner*—Jerome Goldberg

[57] ABSTRACT

The invention is drawn to a novel use of a group of known compounds with the formula shown below,

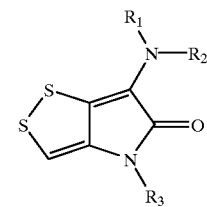

wherein $R_1$, $R_2$=hydrogen, substituted or unsubstituted alkyl, cycloalkyl, acyl, aryl, aralkyl, or heterocyclic group; $R_3$=hydrogen, alkyl, cycloalkyl, aralkyl, aryl or heterocyclic group, the salts thereof, the compositions thereof and their use as medicaments, particularly in the treatment of human and animal cancers.

13 Claims, No Drawings

ANTICANCER PROPERTY OF DITHIOLOPYRROLONES

This is a continuation of application of Ser. No. 08/716,593 filed Sep. 18, 1996.

SUMMARY OF THE INVENTION

The present invention provides anticancer compositions comprising a group of dithiolopyrrolones, the salts thereof, and methods of using the inventive compounds as anticancer agents.

BRIEF DESCRIPTION OF THE DRAWING

The following figure represents the structural formula of dithiolopyrrolones

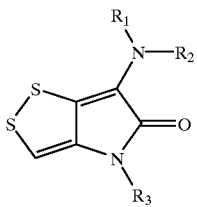

wherein $R_1$, $R_2$=hydrogen, substituted or unsubstituted alkyl, cycloalkyl, acyl, aryl, aralkyl, or heterocyclic group; $R_3$=hydrogen, alkyl, cycloalkyl, aralkyl, aryl or heterocyclic group.

BACKGROUND

Cancer is one of the major causes of death in humans and animals. Millions of people in the world are diagnosed every year as having cancer and a large proportion of these people die of cancer. Despite extensive worldwide effort over many years, cancers continue to be hard-to-treat diseases, and there is an urgent need for more effective anticancer drugs.

Soil organisms have been a traditional source of bioactive materials for the pharmaceutical and agrochemical industry. One of the recent developments has been the commercialization of a soil-living nematode-bacteria combination as a biological control agent against insect pests. A crucial feature of this biocontrol agent is the bioactive nature of the metabolites produced by the bacterial symbiont (Xenorhabdus spp. or Photorhabdus spp.). Some of specific compounds have been isolated from among these bacterial metabolites, they have been identified and their structures elucidated (Forst and Nealson, 1996). Among these identified compounds, several are dithiolopyrrolones.

Dithiolopyrrolones were initially isolated from Streptomyces spp. in the 1940s and from other organisms since that time. This group of compounds includes aureothricin, thiolutin, holomycin and xenorhabdins (Umezawa et al., 1948; Eisenman et al., 1953; Celmer and Solomons, 1955; von Daehne et al., 1969; McInerney et al., 1991). Thiomarinols A, C, D, E, F and G, another group of antibiotics with dithiolopyrrolone ring, were isolated from a marine bacterium, *Alteromonas rava* sp., and their hydrolyzed products with the same heterocyclic ring were obtained by hydrolysis (Shiozawa et al., 1997, J. Antibiotics 50: 449–452). Many additional, diversified compounds with the dithiolopyrrolone ring were also synthesized (WO 94/28001 and WO 94/26750). These compounds possess antimicrobial activity against a wide range of micro-organisms. Among these compounds, thiolutin is the one that has been studied most extensively. Thiolutin inhibits RNA polymerase synthesis (Jimenez et al., 1973; Tipper, 1973), has membrane stabilization activity and inhibits platelet aggregation in vitro (Ninomiya et al., 1980).

Animal cells undergo various enzymatic and biochemical changes when influenced by external chemical factors. For example, when animal cells are challenged by carcinogens or other chemicals many enzymatic and biochemical activities are promoted, and some of the promoted activities, such as those associated with ornithin decarboxylase (ODC) and glutathione, can be experimentally detected. ODC is a rate-limiting enzyme in the synthesis of polyamines which appears to be a prerequisite for cell proliferation, differentiation and neoplastic transformation. One role of glutathione is the protection of cellular macromolecules against reactive intermediates and free radicals. It has been reported (Sharma et al., 1994) that thiolutin inhibits OCD and induces the reduction of glutathione. Other researchers (Menta and Moon, 1991; Arnold et al., 1995) have reported that thiolutin inhibits the promotion of several other activities possibly associated with the occurrence of carcinogenesis in mammary cells that have been exposed to carcinogens. This suggests that thiolutin might have a chemopreventive activity in preventing the initiation of cell transformation from pre-malignant to malignant cancer cells.

Although the study of dithiolopyrrolones has proceeded for about 50 years, the anticancer activity of thiolutin and other dithiolopyrrolones against malignant cells has not been evaluated and reported until now. The anticancer capability of the dithiolopyrrolones and the novel utility of these compounds are the objectives of the present invention.

DESCRIPTION OF THE INVENTION

Several dithiolopyrrolones have been reported to date, and these include aureothricin, thiolutin, holomycin and xenorhabdins. Aureothricin was initially reported by Umezawa et al. (1948), and the structure was fully disclosed by Celmer and Solomons (1955). Thiolutin is produced by *Streptoverticillium album* which is available from the American Type Culture Collection(ATCC), Rockville, Md. (ATCC number of 33049) and several other bacterial species. The production of thiolutin and holomycin by chemical synthesis was published by Hagio and Yoneda (1974) and Stachel, et al. (1992) respectively. The side chains of these compounds can be substituted with various groups, including alkyl, cycloalkyl, acyl, aryl, aralkyl, or heterocyclyl group. The production and antibiotic activity of xenorhabdins was reported and fully disclosed by McInerney et al. (1991) and by Li et al. (1995). The thiomarinols were produced by a marine bacterium, *Alteromonas rava* sp., and their derivatives were obtained by alkaline hydrolysis. Additional, diversified compounds with dithiolopyrrolone ring, wherein $R_1$, $R_2$=hydrogen, substituted or unsubstituted alkyl, cycloalkyl, acyl, aryl, aralkyl, or heterocyclic group; $R_3$=hydrogen, alkyl, aralkyl, aryl, or heterocyclic group were chemically synthesized with well established methods (WO 94/28001, WO 94/26750) and the references cited therein. The examples of dithiolopyrrolones used for the subject invention are prepared by the methods described in the cited references, and the structure of each dithiolopyrrolone derivative has been confirmed by its NMR and MS spectroscopy.

Skilled chemists will be able to use procedures as disclosed herein and others to obtain these dithiolopyrrolones from available stock substances. In carrying out such operations, any suitable filtration, chromatographic, and other purification techniques might be employed by those skilled in the art. A more complete understanding of the invention can be obtained by reference to preferred embodiments of the invention, which are illustrated by the following specific examples and methods of the invention. It will be apparent to those skilled in the art that the examples involve use of materials and reagents that are commercially available from chemical companies, so no details are given respecting them.

Dithiolopyrrolones form salts, therefore, the compounds of the present invention include dithiolopyrrolones and salts thereof. The term "salts", as used herein, denotes acidic and/or basic salts, formed with inorganic and/or organic acids and bases. Suitable acids include, for example, hydrochloric, sulfuric, nitric, benzenesulfonic, acetic, maleic, tartaric and the like, which are pharmaceutically acceptable. While pharmaceutically acceptable salts are preferred, particularly when employing the compounds of the invention as medicaments, other salts find utility, for example, in the production of these compounds, or where non-medicament-type uses are contemplated.

As disclosed herein, dithiolopyrrolones have strong anti-cancer activity against several human cancer cell lines and especially in the treatment of malignant mammary cells. Importantly, dithiolopyrrolones inhibit the growth of HT29 human colon cancer cell lines, the growth of cervical cancer cell line Hela and the MCF-7 breast cancer cell line.

Cancer as a general definition refers to a disease which cells multiply without control and thereby destroying healthy tissues. In a narrow definition, cancer means a malignant growth or tumor in different parts of the human or animal body, that reproduces itself and may spread indefinitely. Many of these tumor cells have been collected and cultured, and their malignant nature is well recognized by the scientific community. Large collections of many cancer cell lines are available for scientific research and development from organizations such as the National Cancer Institute and the American Type Culture Collection in USA. Several of these cell lines such as human colon cancer HT29, cervical cancer Hela and breast cancer MCF-7 were used to demonstrate the anticancer properties of the dithiolopyrrolones in the present invention.

The present invention provides methods of treating a mammal affected by cancers sensitive to dithiolopyrrolones, which comprises administering to the affected individual a therapeutically effective amount of these compounds, the salts thereof or a pharmaceutical composition thereof. In particular, the compounds and the salts thereof of the invention may be used to treat mammalian colon, cervical and breast cancers.

The present invention also relates to the pharmaceutical preparations which contain an active ingredient of these compounds or a pharmaceutically acceptable salt thereof, as well as the process for its preparation.

Examples of pharmaceutical compositions include any solid (tablets, pills, capsules, granules, powder etc.) or liquid (solutions, suspensions or emulsions) in a suitable composition for oral, topical or parenteral administration. These formulations may contain the pure compound or be in combination with a carrier or some other pharmaceutically active compound. These compositions may need to be sterile when administered parenterally.

The administration of dithiolopyrrolones and the pharmacologically active and physiologically compatible derivatives of the dithiolopyrrolones is useful for treating animals or humans that have, for example, cancer of the colon, cervix, breast and the like using the accepted protocols of the National Cancer Institute. The dosage administered will be dependent upon the identity of the cancer disease; the type of host involved including its age, health and weight; the kind of concurrent treatment, if any; and the frequency of treatment and therapeutic ratio. Illustratively, dosage levels of the administered active ingredients are intravenous, 0.1 to about 200 mg/kg; intramuscular, 1 to about 500 mg/kg; orally, 1 to about 1000 mg/kg; intranasal instillation, 1 to about 1000 mg/kg; and aerosol, 1 to about 1000 mg/kg of host body weight. Expressed in terms of concentration, an active ingredient can be present in the compositions of the present invention for localized use about the cutis, intranasally, pharyngolaryngeally, bronchially, bronchiolially, intravaginally, rectally, or ocularly in a concentration from about 0.01 to about 50% w/w of the composition; preferably about 1 to about 20% w/w of the composition; and for parenteral use in a concentration of from about 0.05 to about 50% w/v of the composition and preferably from about 5 to about 20% w/v. The dithiolopyrrolones, as active ingredients to be employed as anticancer agents, can be easily prepared in such unit dosage form with the employment of pharmaceutical materials which themselves are available in the art and can be prepared by established procedures.

To further assist in the understanding of the present invention the following examples are presented to more clearly disclose the present invention and not by way of limitation.

EXAMPLE 1

Identification, and Spectroscopic Data of Some Selected Dithiolopyrrolones Used

NMR spectra were recorded on a Bruker WM400 spectrometer in $CDCl_3$ or $DMSO-d_6$. Low resolution mass spectra were obtained on a Hewlett-Packard 5985B GC/MS system operating at 70 eV using a direct probe. (Abbreviations used as follows: EI=Electron Impact, $M^+$=Molecular Ion, t=triplet, J=coupling constant, Hz=Hertz, d=doublet, m=multiplet).

N-(4,5-dihydro-4-methyl-5-oxo-1,2-dithiolo[4,3-b]pyrrol-6-yl)acetamide, (Thiolutin), XN0: $^1$HNMR ($DMSO-d_6$) δ 2.05 (3H, s), 3.92 (3H, s), 7.19 (1H, s) and 9.85 (1H, broad s); EIMS m/e 228 ($M^+$), 186.

N-(4,5-dihydro-4-methyl-5-oxo- 1,2-dithiolo[4,3-b]pyrrol-6-yl)hexanoamide, XN1: $^1$HNMR ($CDCl_3$) δ 0.90 (3H, t, J=6.9 Hz), 1.35 (4H, m), 1.70 (2H, m), 2.35 (2H, t, J=7.4 Hz), 3.35 (3H, s), 6.63 (1H, s) and 7.43 (1H, broad s); EIMS m/e 284 ($M^+$), 186.

N-(4,5-dihydro-5-oxo-1,2-dithiolo[4,3-b]pyrrol-6-yl)5-methylhexanoamide, XN3: $^1$HNMR ($CDCl_3$) δ 0.89 (6H, d, J=6.6 Hz), 1.24 (3H, m), 1.70 (2H, m), 2.32 (2H, t, J=7.6 Hz), 6.74 (1H, s), 7.44 (1H, broad s) and 7.94 (1H, broad s); EIMS m/e 284 ($M^+$), 172.

EXAMPLE 2

Dithiolopyrrolones as Anticancer Agents

The anticancer activity of a particular dithiolopyrrolone can be demonstrated by standard assays. These assays are commonly used by those skilled in the art and are accepted as indicative of anticancer activity in mammals. The anticancer activities of dithiolopyrrolones have been determined in cell cultures of human colon cancer cell line HT-29, breast cancer cell line MCF-7 and cervical cancer cell line Hela. The procedure was carried out using the method described by Skehan et al. (1990). Briefly, cancer cells were grown in RPMI-1640 medium with glutamine and 10% fetal calf serum, and were harvested from exponential-phase maintenance cultures. The harvested cells were counted and dispensed into replicate 96-well culture plates in 180 μl volumes for each well with a cell density of 2,500 cells/well. The cells were allowed to settle for about 4 hours at 37° C. Then 20 μl of medium containing the test dithiolopyrrolone was added into each well, resulting in a final test compound concentration between 0.008–1 μg/ml. The test plates were then incubated at 37° C. The test was terminated 3 days after incubation by adding to each well 50 μl of cold 50% trichloroacetic acid. The cells were fixed for an hour at 4° C. and then washed five times with tap water. The washed plates were air-dried and stained for 30 minutes with 0.4%

(wt/vol) sulforhodamine B (SRB) which was dissolved in 1% acetic acid. At the end of the staining period, the SRB was removed and plates were quickly rinsed, five times with 1 % acetic acid. After being rinsed, the plates were air-dried and 100 μl of 10 mM tris base (pH 10.5) were added to each well to solubilize the dye bound to the cells. The plates were placed on a gyratory shaker and shaken (100 rpm) for 10 minutes. Finally, the plates were read in a microtiter plate reader at 570 nm. All the dithiolopyrrolones tested exhibited very strong anticancer activity against three cancer cell lines (see table below).

| Dithiolopyrrolone derivatives | Anticancer activity $IC_{50}$ (μg/ml) Cancer cell lines | | |
|---|---|---|---|
| | HT29 | MCF-7 | Hela |
| XN0 | 0.03 | 0.08 | 0.07 |
| XN1 | 0.03 | 0.16 | 0.13 |
| XN3 | 0.03 | 0.11 | 0.09 |

From the foregoing embodiments and examples, it is apparent that an invention has been herein described and illustrated.

While our above description contains many specificities, these should not be construed as limitations on the scope of the invention, but rather as examples of preferred embodiments. Accordingly, the scope of the invention should not be determined by the embodiments presented, but by the appended claims and their legal equivalents.

REFERENCES CITED

Arnold, J. T. et al., 1995. *Cancer Research* 55:537–543.
Celmer, W. D. and I. A. Solomons 1955. *J. Amer. Chem. Soc.* 77:2861–2865.
Eisenman, W. et al., 1953. *Antibiotics and Chemotherapy* 3: 385–392.
Forst, S. and K. Nealson, 1996. *Microbiol. Rev.* 60:21–43.
Hagio, K. and Yoneda, N. 1974. *Bull. Chem. Soc. Japan.* 47:1484–1489.
Jimenez, A. et al., 1973. *Antimicrob. Ag. Chemother.* 729–738.
Li, J. et al., 1995. *J. Nat. Prod.* 58:1081–1085.
McInerney, B. V. et al., 1991. *J. Nat. Prod.* 54:774–784.
Menta, R. G. and R. C. Moon, 1991. *Anticancer Research* 11:593–596.
Ninomiya, Y. T. et al., 1980. *Chem. Pharm. Bull.* 28:3157–3162.
Sharma, S. et al., 1994. *Cancer Research* 54:5848–5855.
Skehan, P. et al., 1990. *J. Natl. Cancer Inst* 82:1107–1118.
Stachel, H.D. et al. 1992. *Liebigs Ann. Chem.* 473–480.
Tipper, D. J. 1973. *J. Bacteriol.* 116:245–256.
Umezawa, H. et al. 1948. *Jap. Med. J.* 1:512–517.
von Daehne, W. et al., 1969. *J. Antibiotics* 22:233–235.
Shiozawa et al., 1997, *J. Antibiotics* 50:449–452.
Baggaley et al. WO 94/28001.
Baggaley et al. WO 94/26750.

We claim:

1. A method for treating a cancer sensitive to dithiolopyrrolones, comprising administrating to a subject in need of such treatment, an effective amount of a compound of the structure shown below,

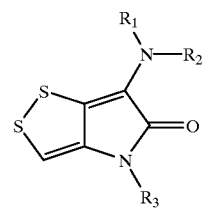

wherein:
$R_1$=hydrogen, lower alkyl, lower cycloalkyl, aryl, or lower aralkyl;
$R_2$=hydrogen, lower alkyl, lower acyl, lower cycloalkyl, aryl, or lower aralkyl; and,
$R_3$=hydrogen, lower alkyl, lower cycloalkyl, lower aralkyl, or aryl,
or a pharmaceutically acceptable salt thereof.

2. The method of claim 1, wherein:
$R_1$=hydrogen, lower alkyl, lower cycloalkyl, aryl, or lower aralkyl;
$R_2$=lower acyl; and,
$R_3$=hydrogen, lower alkyl, lower cycloalkyl, lower aralkyl.

3. The method of claim 1, wherein:
$R_1$=hydrogen;
$R_2$=lower acyl; and,
$R_3$=hydrogen, or methyl.

4. The method of claim 1, wherein:
$R_1$=hydrogen;
$R_2$=acyl group with a straight or branched one to ten carbon chain; and,
$R_3$=hydrogen, or methyl.

5. The method according to claim 1, wherein said cancer is selected from the group consisting of colon, cervical and breast cancer.

6. The method of claim 1, wherein:
$R_1$=H;
$R_2$=$COCH_3$; and,
$R_3$=$CH_3$.

7. The method of claim 1, wherein:
$R_1$=H;
$R_2$=$COC_5H_{11}$; and,
$R_3$=$CH_3$.

8. The method of claim 1, wherein:
$R_1$=H;
$R_2$=$COCH_2CH_2CH_2CH(CH_3)_2$; and,
$R_3$=H.

9. The method of claim 1, wherein:
$R_1$=H.

10. The method of claim 1, wherein:
$R_3$=$CH_3$.

11. The method of claim 1, wherein:
$R_2$=$COCH_3$.

12. The method of claim 1, wherein:
$R_2$=$COC_5H_{11}$.

13. The method of claim 1, wherein:
$R_2$=$COCH_2CH_2CH_2CH(CH_3)_2$.

* * * * *